United States Patent [19]

Maulding et al.

[11] Patent Number: 4,988,824
[45] Date of Patent: Jan. 29, 1991

[54] PROCESS FOR THE PREPARATION OF 23-(C1-C6 ALKYLOXIME)-LL-F28249 COMPOUNDS

[76] Inventors: Donald R. Maulding, 57 Katydid Dr., Somerville, N.J.; Anil Kumar, 36-C Needham Way, Princeton, N.J.

[21] Appl. No.: 405,793
[22] Filed: Sep. 11, 1989
[51] Int. Cl.$^5$ ........................................... C07D 313/06
[52] U.S. Cl. ..................................................... 549/264
[58] Field of Search ......................................... 549/264
[56] References Cited

U.S. PATENT DOCUMENTS 4,201,861 5/1980 Mrozik et al. ........................ 536/7.1
4,855,317 8/1989 Gehret ................................. 549/264

FOREIGN PATENT DOCUMENTS 259779 3/1988 European Pat. Off. ............. 549/264

2176182 12/1980 United Kingdom ................ 549/264

OTHER PUBLICATIONS

Carey and Sandberg, "Advanced Organic Chemistry", 2nd Ed., Pat. B, pp. 481–490, Plenum Press, New York, (1983).
J. Albright et al., *J. Am. Chem. Soc.*, "Dimethylsulfoxide-Acitic Anhydride Mixture for the Oxidation of Alcohols", 89(10), pp. 2416–2423, (1967).

Primary Examiner—Glennon H. Hollrah
Assistant Examiner—Mark W. Russell
Attorney, Agent, or Firm—Carmella A. O'Gorman

[57] ABSTRACT

There is provided a process for the preparation of 23-($C_1$-$C_6$alkyloxime)-LL-F28249 compounds via the oxidation of crystalline 5-O-p-nitrobenzoyl-LL-F28249 compounds.

20 Claims, No Drawings

PROCESS FOR THE PREPARATION OF 23-(C1-C6 ALKYLOXIME)-LL-F28249 COMPOUNDS

BACKGROUND OF THE INVENTION

The present invention relates to a process for the manufacture of 23-($C_1$–$C_6$alkyloxime)-LL-F28249 compounds. The designation LL-F28249 is used to describe a series of compounds produced by the fermentation broth of *Streptomyces cyaneogriseus* subspecies *noncyanogenus*, deposited in the NRRL collection under deposit accession number 15773.

It is an object of this invention to provide a process for the manufacture of 23-($C_1$–$C_6$alkyloxime)-LL-F28249 compounds and more specifically 23-(methyloxime)-LL-F28249α (moxidectin), a potent endectocidal agent.

SUMMARY OF THE INVENTION

The present invention relates to a process for the preparation of 23-($C_1$–$C_6$alkyloxime)-LL-F28249 compounds which comprises protecting the 5-hydroxy group of LL-F 28249 compounds with p-nitrobenzoyl chloride to give the corresponding 5-O(p-nitrobenzoyl)-LL-F28249 compound; oxidizing said compound to give a 5-O(p-nitrobenzoyl)-23-oxo-LL-F28249 derivative in a crystalline state; reacting said derivative with a $C_1$–$C_6$alkoxylamine or salt thereof to give the 23-($C_1$–$C_6$alkyloxime)5-O(p-nitrobenzoyl)-LL-F28249 intermediate in a crystalline state; and deprotecting said intermediate in the presence of base to give the desired 23-($C_1$–$C_6$alkyloxime)-LL-F28249 compound. Optionally, the crystalline 5-O(p-nitrobenzoyl-23-oxo-LL-F28249 derivatives are deprotected in the presence of base to give the corresponding 23-oxo-LL-F28249 compounds and said compounds are reacted with a $C_1$-$C_6$alkoxylamine, or salt thereof, to give the desired 23-($C_1$–$C_6$alkyloxime)-LL-F28249 compound The 23-($C_1$—$C_6$alkyloxime)-LL-F28249 compounds and their use as anthelmintic, insecticidal, nematicidal, ectoparasiticidal and acaricidal agents are described in co-pending U.S. patent application Ser. Nos. 907,283, filed Sept. 12, 1986, and 088,953, filed on Aug. 27, 1987, and are incorporated herein by reference thereto. The antibiotic compounds designated LL-F28249 are described in co-pending U.S. patent application Ser. No. 617,650, filed on June 5, 1984, and incorporated herein by reference thereto.

DESCRIPTION OF THE INVENTION

The invention herein described relates to a process for the manufacture of 23-($C_1$–$C_6$alkyloxime) derivatives of LL-F28249 compounds. The LL-F28249 compounds are represented by the following structural formula

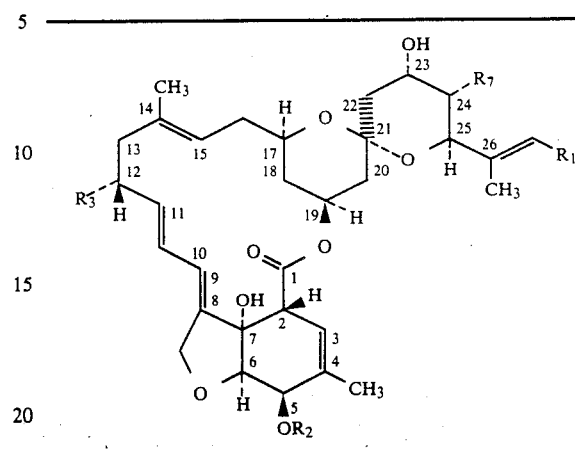

| Component | $R_1$ | $R_2$ | $R_3$ | $R_7$ |
|---|---|---|---|---|
| LL-F28249α | $CH(CH_3)_2$ | H | $CH_3$ | $CH_3$ |
| LL-F28249β | $CH_3$ | H | $CH_3$ | $CH_3$ |
| LL-F28249γ | $CH_3$ | $CH_3$ | $CH_3$ | $CH_3$ |
| LL-F28249ε | $CH(CH_3)_2$ | H | H | $CH_3$ |
| LL-F28249ζ | $CH_2CH_3$ | H | $CH_3$ | $CH_3$ |
| LL-F28249θ | $CH(CH_3)_2$ | H | $CH_3$ | $CH_2CH_3$ |
| LL-F28249ι | $CH(CH_3)_2$ | H | $CH_2CH_3$ | $CH_3$ |
| LL-F28249λ | $CH(CH_3)_2$ | $CH_3$ | $CH_3$ | $CH_3$ |

There is provided a process for the manufacture of 23-($C_1$–$C_6$alkyloxime)-LL-F28249 compounds wherein $R_2$ is hydrogen which comprises protecting the 5-hydroxy group of said LL-F28249 compounds with p-nitrobenzoyl chloride to yield the corresponding 5-O (p-nitrobenzoyl)-LL-F28249 compound; oxidizing said compound to yield the 5-O(p-nitrobenzoyl)-23-oxo-LL-F28249 derivative in a crystalline state; reacting said derivative with a $C_1$–$C_6$alkoxyamine or salt thereof to yield the 23-($C_1$–$C_6$alkoxamine)-5-O(p-nitrobenzoyl)-LL-F28249 intermediate in a crystalline state; and deprotecting said intermediate in the presence of base to yield the desired 23-($C_1$–$C_6$alkyloxime)-LL-F28249 compound. There is further provided a process for the manufacture of 23-($C_1$–$C_6$alkyloxime)-LL-F28249 compounds wherein the crystalline 5-O(p-nitrobenzoyl)-23-oxo-LLF28249 derivatives are deprotected in the presence of base to yield the corresponding 23-oxo-LL-F28249 compounds end said compounds are reacted with a $C_1$–$C_6$alkoxylamine or salt thereof to yield the desired 23-($C_1$–$C_6$alkyloxime)-LL-F28249 compound.

Using LL-F28249α as starting material and methoxylamine hydrochloride as the $C_1$–$C_6$alkoxylamine reagent, the processes of the invention can be illustrated as shown in flow diagram I wherein PNB designates the functionality p-nitrobenzoyl.

FLOW DIAGRAM I

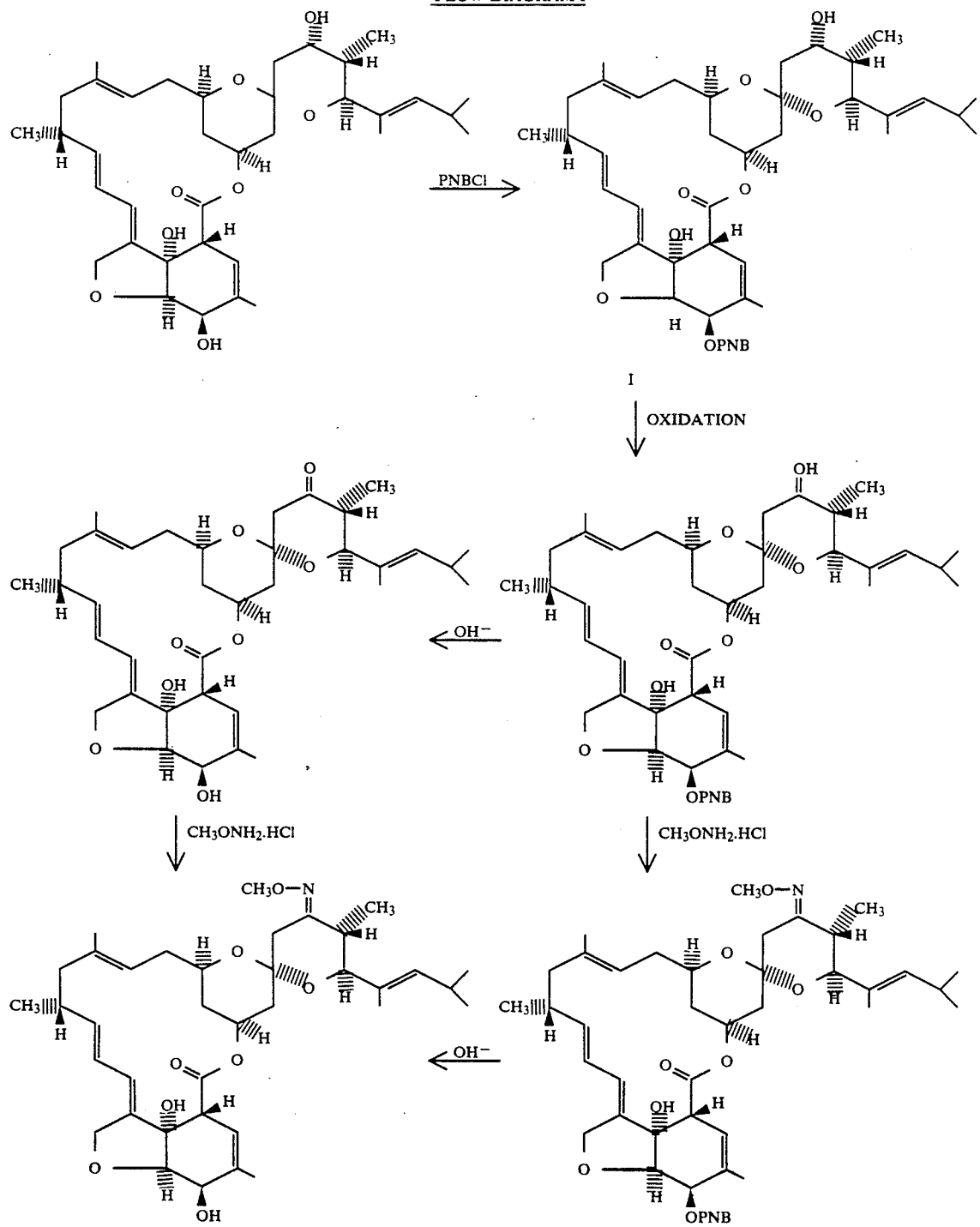

Protection of the 5-hydroxy group of LL-F28249α is achieved by the reaction of LL-F28249α with p-nitrobenzoyl chloride in the presence of an organic solvent such as toluene, methylene chloride, ethyl acetate, acetonitrile and the like, preferably toluene, and an organic base such as pyridine, triethylamine, N-methylpyrrolidone, and the like, preferably triethylamine.

Surprisingly, it has been found that oxidation of 5-O(p-nitrobenzoyl)-LL-F28249 compounds gives a crystalline product, the corresponding 5-O(p-nitrobenzoyl)-23-oxo-LL-F28249 compound A crystalline intermediate allows a simplified, efficient purification of said intermediate via recrystallization from a suitable organic solvent and eliminates complex, time consuming purification by procedures such as column chromatography. Oxidation of the 5-O(p-nitrobenzoyl)-LL-F28249 compound is successfully achieved using an oxidizing system selected from the group consisting of pyridinium dichromate and acetic anhydride; pyridinium dichromate and dimethylformamide; aluminum t-butoxide and o-benzoquinone; phosphorous pentoxide and dimethyl sulfoxide; dicyclohexylcarbodiimide and dimethyl sulfoxide; manganese dioxide; and acetic andydride and dimethyl sulfoxide.

A preferred oxidizing system for the oxidation of 5-O(p-nitrobenzoyl)-LL-F28249 compounds is manganese dioxide in the presence of a solvent such as methylene chloride, acetonitrile, ethyl acetate or the like, preferably ethyl acetate.

A more preferred oxidizing system for the oxidation of 5-O(p-nitrobenzoyl)-LL-F28249 compounds is acetic anhydride and dimethyl sulfoxide in the presence of pyridine and an acid such as acetic acid, trifluoroaceic acid, dichloroacetic acid, monochloroacetic acid and the like, preferably monochloroacetic acid. Surprisingly, it has been found that the use of acetic anhydride and dimethyl sulfoxide in the presence of pyridine and an acid greatly enhances the yield of the 5-O(p-nitrobenzoyl)-23-oxo-LL-F28249 derivatives over the use of acetic anhydride and dimethyl sulfoxide alone. For example, the acetic anhydride and dimethyl sulfoxide oxidation is carried out in the presence of pyridine and monochloroacetic acid, the yield of 5-O(p-nitrobenzoyl)-23-oxo-LL-F2849α is 76%; whereas when the same oxidation is carried out without the presence of pyridine and monochloroacetic acid, the yield is 2–4%.

Optionally, the crystalline 5-O(p-nitrobenzoyl)-23-oxo-LL-F28249 derivative is purified by recrystallization from a suitable solvent (preferably n-propanol) prior to deprotection (removal of the p-nitrobenzoyl group) or reaction with $C_1$-$C_6$alkoxylamine hydrochloride.

Preferably, a solution of the crude reaction product, 5-O(p-nitrobenzoyl)-23-oxo-LL-F28249 compound, in an organic solvent, such as toluene, is reacted with an aqueous solution of $C_1$-$C_6$alkoxylamine hydrochloride and sodium acetate and stirred until oxime formation is complete. The thus-formed 23-($C_1$-$C_6$alkyloxime)-5-O(p-nitrobenzoyl)-LL-F28249 intermediate is isolated and then purified by recrystallization from a suitable solvent, preferably n-butanol.

The recrystallized 23-($C_1$-$C_6$alkyloxime-5-O(p-nitrobenzoyl)-LL-F28249 compound is deprotected by reaction with sodium hydroxide at 0°–25° C. to give the desired 23-($C_1$-$C_6$alkyloxime)-LL-F28248 product. The deprotection is achieved by reacting a solution of a 23-($C_1$-$C_6$alkyloxime)-5-O(p-nitrobenzoyl)-LL-F28249 compound in an organic solvent such as toluene, dioxane, n-butanol or the like, preferably dioxane, with an aqueous solution of sodium hydroxide at 0°–25° C. and isolating the product 23-($C_1$-$C_6$alkyloxime)-LLF28249 compound from the organic phase using standard procedures such as concentration and filtration or removal of the solvent.

In order to facilitate a further understanding of the invention, the following examples are presented primarily for the purpose of illustrating more specific details thereof. The invention is not to be limited thereby except as defined in the claims.

Unless otherwise noted, all parts are by weight, all high pressure liquid chromatographic analyses are designated as HPLC analyses, and all proton nuclear magnetic spectroscopic analyses are designated as $^1$HNMR analyses.

EXAMPLE 1

Preparation of 5-O-(p-nitrobenzoyl)-LL-F28249α

A stirred solution of LL-F28249α (6.36 g, 10.4 mmole) in methylene chloride is treated with pyridine (1.98 g, 25.0 mmole) and p-nitrobenzoyl chloride (2.45 g, 13.2 mmole) at 20°–25° C. After 4 hours at 2°–25° C., the reaction mixture is treated with saturated sodium bicarbonate and methylene chloride and stirred until solution is complete. The phases are separated, the organic phase is washed sequentially with saturated sodium bicarbonate, 5% hydrochloric acid, and seturated sodium chloride and concentrated in vacuo to give the title compound as a solid foam, 7.9 g (quantitative yield) identified by liquid chromatography, $^1$HNMR and mass spectral analyses.

EXAMPLE 2

Preparation of 5O-(p-nitrobenzoyl)-LL-F28249α

A stirred solution of LL-F28249α (6.13 g, 10.0 mmoles) in toluene is treated with triethylamine (2.53 g, 25 mmole), cooled to 15° C., treated portionwise with p-nitrobenzoyl chloride (2.60 g, 14 mmole) at a temperature range of 15°–22° C., and stirred for 6 hours at 20°–24° C. The reaction mixture is treated with water, stirred for 10 minutes and filtered. The filtrate is separated, the organic phase is washed sequentially with saturated sodium bicarbonate, 3N hydrochloric acid and water, and concentrated in vacuo to give the title product as a solid foam, 7.55 g.

EXAMPLE 3

Preparation of 5-O(p-nitrobenzoyl)-23-oxo-LL-F28249α using pyridinium dichromate and dimethylformide A stirred solution of 5-O(p-nitrobenzoyl)-LL-F28249α (3.12 g, 4.10 mmole) in dimethylformamide is treated with pyridinium dichromate (18.8 g, 50 mmole) in a single portion, stirred at 20°–25° C. for 6 hours and poured into water. The reaction mixture is stirred for 15 minutes and filtered. The filter cake is washed with water, air-dried and taken up in ethyl acetate. The resulting mixture is heated at reflux temperature for 15 minutes, treated with diatomaceous earth and filtered. The filtrate is concentrated in vacuo to give a red-brown solid which is recrystallized from n-propanol to give the title product as white crystals, 3.33 g (52% overall yield from LL-F28249α) mp 217°–221° C. identified by $^1$HNMR and mass spectral analyses.

EXAMPLE 4

Preparation of 5-O(p-nitrobensoyl)-23-oxo-LL-F28249α using pyridinium dichromate and acetic anhydride.

A solution of 5-O(p-nitrobenzoyl)-LL-F28249α (0.38 g, 0.5 mmol) in methylene chloride is added to a freshly prepared mixture of pyridinium dichromate (0.19 g, 0.5 mmol) and acetic anhydride (0.3g, 3.0 mmol) with vigorous stirring. The reaction mixture is stirred at room temperature for 15 minutes, heated at reflux temperature for 6–8 hours, cooled to room temperature, and treated with water. After vigorous stirring, the phases are separated and the organic phase is washed with saturated sodium bicarbonate solution and concentrated in vacuo to give a residue. The residue is taken up in ethyl acetate and chromatographed using silica gel and ethyl acetate as eluent to give a pale yellow/grey solid. This solid is stirred with ethyl acetate; hexanes (55:45 v/v) filtered, and the filtrate is concentrated in vacuo to give the title compound as a pale yellow solid, 0.26 g, identified by $^1$HNMR and HPLC analyses.

EXAMPLE 5

Preparation of
5-O(p-nitrobenzoyl)-23-oxo-LL-F28249α using
phosphorous pentoxide and dimethyl sulfoxide A stirred mixture of 5-O(p-nitrobenzoyl)-LL-F28249α (0.38 g, 0.50 mmole), aluminum t-butoxide (0.184 g, 0.75 mmole) and o-benzoquinone (0.216 g, 2.0 mmole) in toluene is heated at reflux temperature for 2 hours, cooled to room temperature, treated with toluene and dilute sulfuric acid (16%), stirred for 5 minutes and filtered. The filtrate is separated and the organic phase is washed with water and concentrated in vacuo to give a glassy solid residue. The residue is taken up in ethyl acetate end filtered through neutral alumina. The filtrate is concentrated in vacuo to give the title product as a white solid, 0.324 g, (71% yield by HPLC analyses).

EXAMPLE 6

Preparation of 5-O(p-nitrobenzoyl)-23-LL-28249α
using phosphorous pentoxide and dimethyl sulfoxide A solution of 5-O(p-nitrobenzoyl)-LL-F28249α (0.38 g, 0.50 mmoles) and dimethyl sulfoxide (0.75 g, 9.6 mmoles) in methylene chloride is treated with powdered phosphorous pentoxide (0.107 g, 0.75 mmole) in one portion, stirred at 20°-25° C. for 19 hours, treated dropwise with triethylamine (0.30 g, 3.0 mmole), stirred for 30 minutes, treated further with methylene chloride and water and stirred for 5 minutes. The phases are separated and the organic phase is washed with dilute hydrochloric acid (7%) and concentrated in vacuo to give the title product as a white solid, 0.28 g (47% purity by HPLC analysis).

EXAMPLE 7

Preparation of
5-O-(p-nitrobenzoyl)-23-oxo-LL-F28249α via
manganese dioxide using methylene chloride as solvent A solution of 5-O(p-nitrobenzoyl)-LL-F28249α (0.19 g, 0.25 mmole) in methylene chloride is treated with manganese dioxide (8.0 g, 92 mmoles), stirred at 20°-25° C. for 2 hours, treated further with methylene chloride, stirred for 5 minutes and filtered. The filtrate is concentrated in vacuo to give the title compound as a white solid, 0.08 g, 51% purity by HPLC analysis.

EXAMPLE 8

Preparation of
5-O(p-nitrobenzoyl)-23-oxo-LL-F28249α via
manganese dioxide using acetonitrile as solvent A solution of 5-O(p-nitrobenzoyl)-LL-F28249α (0.19 g, 0.25 mmole) in acetonitrile is treated with manganese dioxide (8.0 g, 92 mmoles), stirred for 3 hours at room temperature, treated further with acetonitrile, stirred for 5 minutes and filtered. The filter cake is slurried in methylene chloride and filtered. The acetonitrile and methylene chloride filtrates were combined, washed with water and concentrated in vacuo to give the title compound as a white solid, 0.14 g, 69% purity by HPLC analysis.

EXAMPLE 9

Preparation of
5-O(p-nitrobenzoyl)-23-oxo-LL-F28249α via
manganese dioxide and using ethyl acetate as solvent A solution of 5-O(p-nitrobenzoyl)-LL-F28249α (1.0 g, 1.3 mmole) in ethyl acetate is treated With manganese dioxide (20.0 g, 230 mmole), stirred at 2°-25° C. for 3 hours and filtered. The filter cake is washed with ethyl acetate. The filtrates are combined, treated with manganese dioxide (8.0 g, 92 mmole), stirred at 2°-25° C. for 3 hours and filtered. The filter cake is washed with ethyl acetate; the filtrates are combined and concentrated in vacuo to give the title product as a white solid, 0.8 g, (70% purity by HPLC analysis). The solid is recrystallized from n-propanol to give white crystals, mp 218°-222° C.

EXAMPLE 10

Preparation of
5-O(p-nitrobenzoyl)-23-oxo-LL-F28249α via
dicyclohexylcarbodiimide and dimethyl sulfoxide A solution of 5-O(p-nitrobenzoyl)-LL-F28249α (0.38 g, 0.50 mmole) in benzene is treated sequentially with dimethyl sulfoxide (0.78 g, 10 mmole), pyridine (0.04 g, 0.5 mmole) trifluoroacetic acid (0.31 g, 0.25 mmole) and dicyclohexylcarbodiimide (0.31 g, 1.5 mmole), stirred at 20°-25° C. for 21 hours, treated further with benzene and filtered. The filter cake is washed with benzene. The combined filtrates are washed with water and concentrated in vacuo to give the title compound as a light orange-brown solid, 0.34 g, 75% yield by HPLC analysis.

EXAMPLE 11

Preparation of
5-O(p-nitrobenzoyl)-23-oxo-LL-F28249α via acetic
anhydride and dimethyl sulfoxide in the presence of
pyridinium trifluoroacetate A mixture of 5-O(p-nitrobenzoyl)-LL-F28249α (0.38 g, 0.5 mmole), dimethyl sulfoxide (0.78 g, 10 mmole) and pyridinium trifluoroacetate (0.97 g, 0.5 mmole) in ethyl acetate is treated dropwise with acetic anhydride (0.26 g, 2.5 mmole), stirred for 24 hours at 20°-25° C. and treated with ethyl acetate and water. The phases are separated; the organic phase is washed with water and concentrated in vacuo to give a viscous oil residue. The residue is taken up in methylene chloride and concentrated in vacuo to give the title product as a yellow solid, 0.36 g, identified by HPLC analysis.

EXAMPLE 12

Preparation of
5-O(p-nitrobenzoyl)-23-oxo-LL-F28249α via acetic
anhydride and dimethyl sulfoxide in the presence of
pyridine and dichloroacetic acid A mixture of 5-O(p-nitrobenzoyl)-LL-F22849α (7.26 g, 10 mmole) and pyridine (31.6 g, 400 mmole) is treated with dimethyl sulfoxide (15.6 g, 200 mmole) and dichloroacetic acid (1.29 g, 10 mmole), cooled to 2°-3° C., treated dropwise with acetic anhydride (5.1 g, 50 mmole) at 3°-7° C. and treated with methylene chloride and water. The reaction mixture is stirred at ambient temperature for 15-30 minutes and the phases are separated. The organic phase is washed with cold dilute hydrochloric acid (5%), and 5% sodium chloride solution and concentrated in vacuo to give the title product as a yellow solid foam, 7.47 g, 73% purity by HPLC analysis.

Using essentially the same procedure, but varying the acid reagent used, the following yields are obtained and reported in Table I.

stirring the reaction mixture at 15°–20° C. for 10 minutes, the phases are separated. The organic phase is washed sequentially with cold 2.4N hydrochloric acid and water at 15°–20° C. and concentrated in vacuo to give the title product as a yellow solid foam, 1.4 g, 71% purity by HPLC analysis.

TABLE I

Oxidation of 5-O(p-nitrobenzoyl)-LL-F28249alpha to
5-O(p-nitrobenzoyl)-23-oxo-LL-F28249alpha via
Acetic Anhydride and Dimethyl Sulfoxide
In the Presence of Pyridine and An Acid

| Exp. | Molar Equivalents | | | | | | | |
|---|---|---|---|---|---|---|---|---|
| | Dimethyl Sulfoxide | Acetic Anhydride | Pyridine | Acid[a]-Mol eq | | Solvent | Temp (°C.) | Time (h) | % Yield |
| 1 | 20 | 5 | 40 | DCAA | 1.0 | Pyridine | 2–3 | 4 | 76 |
| 2 | 20 | 5 | 40 | DCAA | 0.3 | Pyridine | 2–3 | 4 | 57 |
| 3 | 20 | 4 | 20 | MCAA | 1.0 | Pyridine | 2–3 | 7 | 75 |
| 4 | 20 | 5 | 40 | MCAA | 1.0 | Pyridine | 20–25 | 4 | 51 |
| 5 | 20 | 5 | 40 | TERE | 1.0 | Pyridine | 20–25 | 24 | 55–60 |
| 6 | 20 | 5 | 40 | TCAA | 1.0 | Pyridine | 20–25 | 24 | 40–50 |
| 7 | 20 | 5 | 40 | H3PO4 | 0.8 | Pyridine | 20–25 | 24 | 20–25 |
| 8 | 20 | 5 | 40 | BA | 1.0 | Pyridine | 20–25 | 4 | 15–20 |
| 9 | 20 | 5 | 10 | DCAA | 1.0 | Ethyl acetate | 20–25 | 6 | 66 |
| 10[b] | 20 | 5 | 1 | TFAA | 1.0 | Ethyl acetate | 20–25 | 24 | 60 |
| 11 | 20 | 8 | 22 | DCAA | 1.0 | Ethyl acetate | 20–25 | 3 | 63 |
| 12 | 20 | 3 | 1 | TFAA | 1.0 | Benzene | 20–25 | 6 | 42 |
| 13 | 40 | 5 | 1 | TFAA | 1.0 | Benzene | 20–25 | 8 | 54 |
| 14 | 40 | 5 | 1 | TFAA | 1.0 | Toluene | 20–25 | 24 | 45 |
| 15 | 40 | 3 | 1 | TFAA | 1.0 | CH3Cl2 | 20–25 | 4 | 34 |
| 16 | 40 | 3 | 1 | TFAA | 1.0 | CH2CN | 20–25 | 5 | 20–25 |
| 17 | 40 | 3 | 1 | TFAA | 1.0 | Dimethylformamide | 20–25 | 4 | 20–25 |
| 18 | 40 | 40 | 0 | 0 | | Dimethyl sulfoxide | 20–25 | 16 | 2–4 |

[a]DCAA = dichloroacetic acid, MCAA = monochloroacetic acid, TCAA = trichloroacetic acid, TERE = terephthalic acid, BA = benzoic acid, TFAA = trifluoroacetic acid
[b]Reaction is carried out in the presence of 4A molecular sieves.

EXAMPLE 13

Preparation of
5-O(p-nitrobenzoyl)-23-oxo-LL-F28249α via acetic anhydride and dimethyl sulfoxide in the presence of pyridine and monochloracetic acid A mixture of 5-O(p-nitrobenzoyl)-LL-F28249α (1.52 g, 2.0 mmole) and pyridine (3.16 g, 40 mmole) in toluene is treated with dimethyl sulfoxide (3.12 g, 40 mmole) and monochloroacetic acid (0.19 g, 2.0 mmole), cooled to 2°–3° C., treated dropwise with acetic anhydride (0.82 g, 8.0 mmole) at 3°–5° C., stirred at 2°–3° C. for 7 hours and treated further with toluene and water. After

EXAMPLE 14

Evaluation of the oxidation of
5O-(p-nitrobenzoyl)-LL-F28249α to form
5-O(p-nitrobenzoyl)-23-oxo-LL-F28249α using a variety of oxidizing reagents A variety of oxidizing systems are evaluated for the conversion of 5-O(p-nitrobenzoyl)-LL-F28249α to 5-O(p-nitrobenzoyl)-23-oxo-LL-28249α. The reagents, reaction conditions and percent 5-O(p-nitrobenzoyl)-23-oxo-LL-28249α obtained as determined by HPLC analysis are reported in Table II

TABLE II

Attempted Oxidation of 5-O(p-Nitrobenzoyl)-LL-F28249alpha to
5-O(p-Nitrobenzoyl)-23-oxo-LL-F28249alpha
Using a Variety of Oxidizing Reagents

| Experiment | Oxidant | Molar Equivalents | Solvent | Temp (°C.) | Time (h) | % Product (HPLC area %) |
|---|---|---|---|---|---|---|
| 1 | MoO3 | 0.04 | Toluene | Reflux | 3.5 | 14% |
| | Dimethyl Sulfoxide | 0.80 | | | | |
| 2 | N-Bromosuccinimide | 1.0 | CH3CN | 20–25 | 3 | 10% |
| 3 | K2S2O8 | 1.2 | CH2Cl2/water | 20–25 | 3 | 6% |
| | Bu4NBr | 0.1 | | | | |
| | RuCl3 | 0.2 | | | | |
| 4 | NaOCl | 6.0 | CH2Cl2/water | 20–25 | ca 4 | 0% |
| | Bu4NBr | 0.5 | | | | |
| 5 | (NH4)2Ce(NO3)6 | 10 | Ethyl Acetate | 20–25 | 3 | 0% |
| 6 | KMnO4 | 1.5 | t-Butanol/water | 20–25 | 1 | 0% |
| 7 | KMnO4 | 1.5 | Acetic Acid | 20–25 | 0.5 | 0% |
| 8 | KMnO4 | 1.0 | Acetone | 20–25 | 5 | 0% |
| 9 | KMnO4 | 1.5 | Methylene Chloride | 20–25 | 5 | No reaction |
| | CuSO4.5H2O | 6.0 | | | | |
| 10 | BaMnO4 | 10 | Toluene | Reflux | 6 | 0% |
| 11 | BaMnO4 | 15.0 | Methylene | 20–25 | 6 | No reaction |

TABLE II-continued

Attempted Oxidation of 5-O(p-Nitrobenzoyl)-LL-F28249alpha to
5-O(p-Nitrobenzoyl)-23-oxo-LL-F28249alpha
Using a Variety of Oxidizing Reagents

| Experiment | Oxidant | Molar Equivalents | Solvent | Temp (°C.) | Time (h) | % Product (HPLC area %) |
|---|---|---|---|---|---|---|
| 12 | CH$_2$NEt$_3$Cl<br>BaMnO$_4$ | 0.5<br>15 | Methylene Chloride | 20–25 | 5 | No reaction |
| 13 | Pyridinium Sulfite<br>Dimethyl Sulfoxide | 3.0<br>40.0 | Methylene Chloride | 20–25 | 1 | No reaction |
| 14 | Pyridinium Sulfite<br>Pyridine<br>Trifluoro-acetic acid | 3.0<br>20.0<br>1.0<br>0.5 | Methylene Chloride | 20–25 | 22 | No reaction |
| 15 | H$_2$O$_2$<br>Bu$_4$NBr | 4.0<br>0.1 | Methylene Chloride<br>Water | 20–25 | 5 | No reaction |
| 16 | p-Benzoquinone<br>Alumina | 20 | Benzene | Reflux | 5 | No reaction |

EXAMPLE 15

Preparation of
5-O(p-nitrobenzyl)-23-methyloxime)-LL-F28249α

A solution of 5-O(p-nitrobenzoyl)-23-oxo-LL-F28249α (10.67 g, 14.0 mmole) in n-butanol is treated with a solution of methoxylamine hydrochloride (2.34 g, 28.1 mmole) and anhydrous sodium acetate (2.30 g, 28.1 mmole) in water at 20°–22° C., stirred for 2 hours at 20°–22° C. and filtered. The filter cake is air-dried and recrystallized from n-butanol (filtered hot) to give the title compound as a colorless solid, 3.6 g, 91% purity by HPLC analysis.

EXAMPLE 16

Preparation of
5-O(p-nitrobenzoyl)-23-(methyloxime)-LL-F28249α

A solution of 5-O(p-nitrobenzoyl)-23-oxo-LL-F-28249α (1.5 g, 2.0 mmole) in toluene is treated with a solution of methoxylamine hydrochloride (0.25 g, 3.0 mmol) and anhydrous sodium acetate (0.25 g, 3.0 mmol) in water and stirred at 20°–25° C. for 10 hours. The toluene phase is separated, washed with water and concentrated in vacuo to give a solid residue. The solid is recrystallized from n-butanol to give the title product, 0.65 g, identified by HPLC analysis.

EXAMPLE 17

Preparation of 23-(methyloxime)-LL-F28249α

A solution of 5-O(p-nitrobenzoyl)-z3-(methyloxime)-LL-F28249α (1.58 g, 2.0 mmole) in dioxane is treated dropwise with 4% sodium hydroxide (3.0 g, 3.0 mmole NaOH) at 8°–12° C., stirred for 3 hours at 8°–12° C., treated with toluene and water, and stirred for 5 minutes at ambient temperatures. The phases are separated and the organic phase is washed with 10% sodium chloride and concentrated in vacuo to give the title compound as a white solid foam, 1.15 g, 89% purity by HPLC analysis.

EXAMPLE 18

Preparation of 23-oxo-LL-F28249α

A mixture of 5-O(p-nitrobenzoyl)-23-oxo-LL-F-28249α (1.52 g, 2.0 mmole) and 4% sodium hydroxide (3.3 g, 3.3 mmole NaOH) in dioxane is stirred at 23° C. for 2 hours, treated with toluene and water and shaken. The phases are separated and the organic phase is washed with water and concentrated in vacuo to give the title compound as a solid foam, 0.90 g identified by $^1$HNMR.

EXAMPLE 19

Preparation of 23-(methyloxime)-LL-F28249α

A mixture of 23-oxo-LL-F28249α (0.90 g, 1.5 mmole), methoxylamine hydrochloride (0.42 g, 5.0 mmole), anhydrous sodium acetate (0.41 g, 5.0 mmole), acetic acid and dioxane is stirred at 20°–25° C. for 22 hours, treated with toluene and water and stirred for 5 minutes. The phases are separated, and the organic phase is washed with water and concentrated in vacuo to give the title compound as a solid foam, 0.84 g, 71% purity by HPLC analysis.

What is claimed is:

1. A process for the preparation of a 23-(C$_1$-C$_6$alkyloxime)-LL-F28249 compound which comprises protecting the 5-hydroxy group of a LL-F28249 compound with p-nitrobenzoyl chloride to yield a 5-O(p-nitrobenzoyl)-LL-F28249 compound; oxidizing said compound to yield a 5-O(p-nitrobenzoyl)-23-oxo-LL-F28249 derivative in a crystalline state; reacting said derivative with a C$_1$-C$_6$alkoxylamine or salt thereof to yield a 23-(C$_1$-C$_6$alkyloxime)-5-O(p-nitrobenzoyl)-LL-F28249 intermediate; and deprotecting said intermediate in the presence of base to yield the product 23-(C$_1$-C$_6$alkyloxime)-LL-F28249 compound.

2. A process for the preparation of a 23-(C$_1$-C$_6$alkyloxime)-LL-F28249 compound which comprises protecting the 5-hydroxy group of a LL-F28249 compound with p-nitrobenzoyl chloride to yield a 5-O(p-nitrobenzoyl)-LL-F28249 compound; oxidizing said compound to yield a 5-O(p-nitrobenzoyl)-23-oxo-LL-F28249 derivative in a crystalline state; deprotecting said derivative in the presence of base to yield a 23-oxo-LL-F28249 compound; and reacting said compound with a C$_1$-C$_6$alkoxylamine or salt thereof to yield the product 23-(C$_1$-C$_6$alkyloxime)-LL-F28249 compound.

3. The process according to claim 1, wherein the oxidation is carried out using an oxidizing system selected from the group consisting of acetic anhydride and dimethyl sulfoxide; manganese dioxide; pyridinium dichromate and acetic anhydride; aluminum t-butoxide and o-benzoquinone; phosphorous pentoxide and dimethyl sulfoxide; and dicyclohexylcarbodiimide and dimethyl sulfoxide.

4. The process according to claim 2, wherein the oxidation is carried out using an oxidizing system selected from the group consisting of acetic anhydride and dimethyl sulfoxide; manganese dioxide; pyridinium dichromate and acetic anhydride; aluminum t-butoxide and o-benzoquinone; phosphorous pentoxide and dimethyl sulfoxide; and dicyclohexylcarbodiimide and dimethyl sulfoxide.

5. The process according to claim 3, wherein the oxidizing system is acetic anhydride and dimethyl sulfoxide and the oxidation is carried out in the presence of pyridine and an acid.

6. The process according to claim 4, wherein the oxidizing system is acetic anhydride and dimethyl sulfoxide and the oxidation is carried out in the presence of pyridine and an acid.

7. The process according to claim 5, wherein the acid is monochloroacetic acid.

8. The process according to claim 6, wherein the acid is monochloroacetic acid.

9. The process according to claim 3, wherein the oxidizing system is manganese dioxide and the oxidation is carried out in the presence of ethyl acetate.

10. The process according to claim 4, wherein the oxidizing system is manganese dioxide and the oxidation is carried out in the presence of ethyl acetate.

11. The process according to claim 3, wherein the oxidizing system is pyridinium dichromate and acetic anhydride.

12. The process according to claim 4, wherein the oxidizing system is pyridinium dichromate and acetic anhydride.

13. The process according to claim 1, wherein the 5-O(p-nitrobenzoyl)-23-oxo-LL-F28249 derivative is purified by recrystallization from a suitable solvent.

14. The process according to claim 2, wherein the 5-O(p-nitrobenzoyl)-23-oxo-LL-F28249 derivative is purified by recrystallization from a suitable solvent.

15. The process according to claim 1, wherein the 23-($C_1$-$C_6$alkyloxime)-5O-(p-nitrobenzoyl)-LL-F28249 intermediate is purified by recrystallization from a suitable solvent.

16. The process according to claim 15, wherein the solvent is n-butanol.

17. The process according to claim 1, wherein the LL-F28249 compound is LL-F28249α.

18. The process according to claim 2, wherein the LL-F28249 compound is LL-F28249α.

19. The process according to claim 1, wherein the product compound is 23-(methyloxime)-LL-F28249α.

20. The process according to claim 2, wherein the product compound is 23-(methyloxime)-LL-F28249α.

* * * * *

UNITED STATES PATENT OFFICE
CERTIFICATE OF CORRECTION

Patent No. 4,988,824    Dated January 29, 1991

Inventor(s) Robert H. Maulding et al.

It is certified that error appears in the above-identified patent and that said Letters Patent is hereby corrected as shown below:

Claim 15

Column 14, line 16:
  Claim 15. The process according to claim 1, wherein the 23-($C_1$-$C_6$alkyloxime)-5-O-(p-nitrobenzoyl)-LL-F28249 intermediate is purified by recrystallization from a suitable solvent.

Signed and Sealed this

Twenty-third Day of June, 1992

Attest:

DOUGLAS B. COMER

Attesting Officer    Acting Commissioner of Patents and Trademarks